US012648704B2

(12) United States Patent
Deliwala

(10) Patent No.: US 12,648,704 B2
(45) Date of Patent: Jun. 9, 2026

(54) LOW FREQUENCY NOISE IMPROVEMENT IN PLETHYSMOGRAPHY MEASUREMENT SYSTEMS

(71) Applicant: Analog Devices, Inc., Wilmington, MA (US)

(72) Inventor: Shrenik Deliwala, Andover, MA (US)

(73) Assignee: Analog Devices, Inc., Wilmington, MA (US)

( * ) Notice: Subject to any disclaimer, the term of this patent is extended or adjusted under 35 U.S.C. 154(b) by 1018 days.

(21) Appl. No.: 17/582,842

(22) Filed: Jan. 24, 2022

(65) Prior Publication Data

US 2022/0142584 A1       May 12, 2022

Related U.S. Application Data

(62) Division of application No. 14/500,129, filed on Sep. 29, 2014, now Pat. No. 11,229,373.

(60) Provisional application No. 61/954,301, filed on Mar. 17, 2014.

(51) Int. Cl.
A61B 5/1455        (2006.01)
A61B 5/00          (2006.01)
A61B 5/024         (2006.01)

(52) U.S. Cl.
CPC ...... A61B 5/02433 (2013.01); A61B 5/14551 (2013.01); A61B 5/14552 (2013.01); A61B 5/7203 (2013.01); *A61B 2560/0209* (2013.01)

(58) Field of Classification Search
CPC .................................................... A61B 5/1455
See application file for complete search history.

(56) References Cited

U.S. PATENT DOCUMENTS

| | | | |
|---|---|---|---|
| 5,533,509 A | 7/1996 | Koashi et al. | |
| 7,909,768 B1 | 3/2011 | Turcott | |
| 8,175,668 B1 * | 5/2012 | Nabutovsky ....... | A61N 1/36557 |
| | | | 600/326 |
| 8,195,262 B2 | 6/2012 | Chew et al. | |
| 2010/0041969 A1 | 2/2010 | Beise | |
| 2012/0253159 A1 | 10/2012 | Medina et al. | |
| 2015/0196257 A1 * | 7/2015 | Yousefi .................. | A61B 5/024 |
| | | | 600/324 |

* cited by examiner

*Primary Examiner* — Marjan Fardanesh
(74) *Attorney, Agent, or Firm* — ArentFox Schiff LLP

(57) ABSTRACT

A plethysmography ("PPG") measurement system may include at least one source of PPG radiation and at least one auxiliary sensor for detection of PPG radiation. The radiation source emits a portion of the PPG radiation toward a subject and another portion along an optical path for direct communication between the PPG radiation source and the auxiliary sensor. The auxiliary sensor may develop a profile against which measurements from primary PPG sensors, which receive light returning from the subject, may be compared. From this comparison, new PPG signals may be generated that exhibit lower noise than the PPG signals output by PPG sensors. These noise mitigation techniques may be used advantageously by a PPG system to generate more accurate measurements and also to reduce power consumption by the radiation sources.

20 Claims, 7 Drawing Sheets

FIG. 1A
FIG. 1B
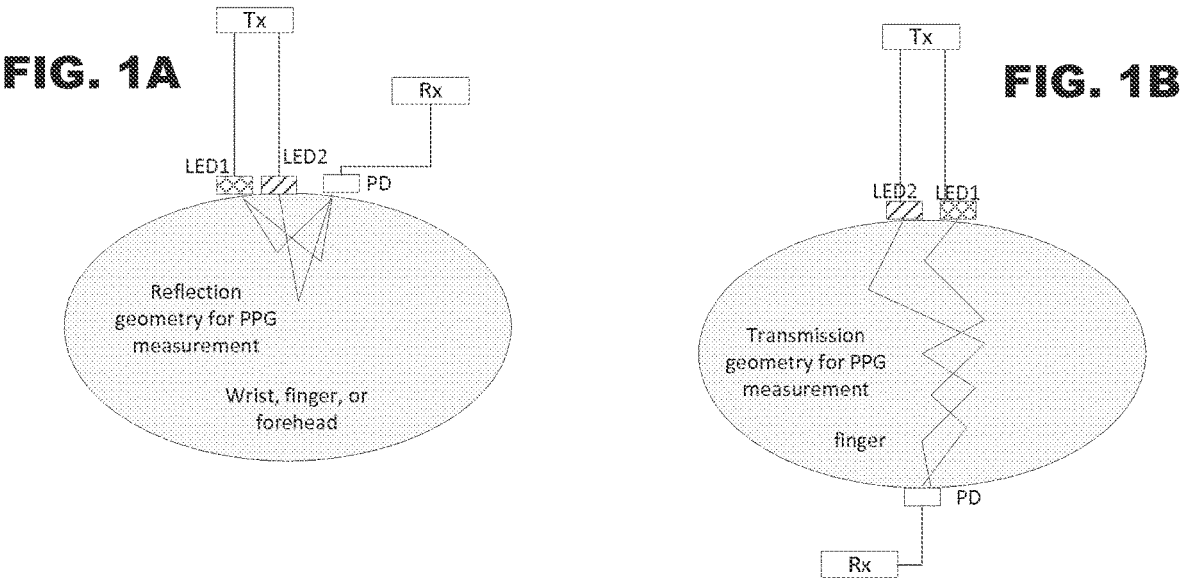
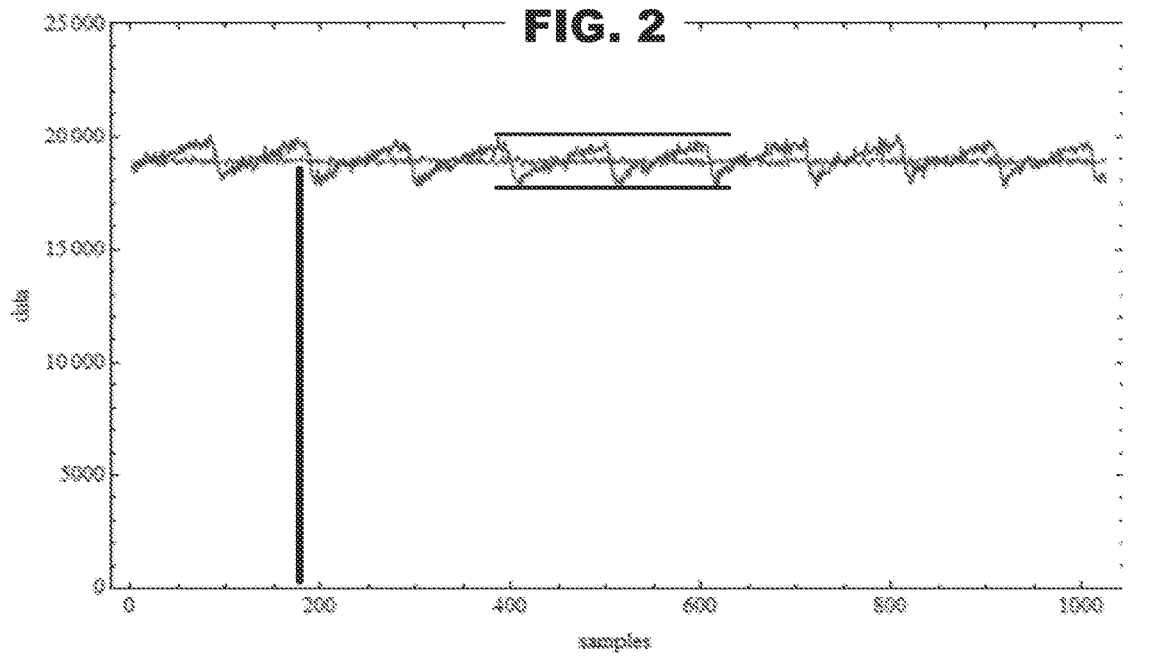
FIG. 2

*300*

*400*

900

900

900

1000

FIG. 11
1100
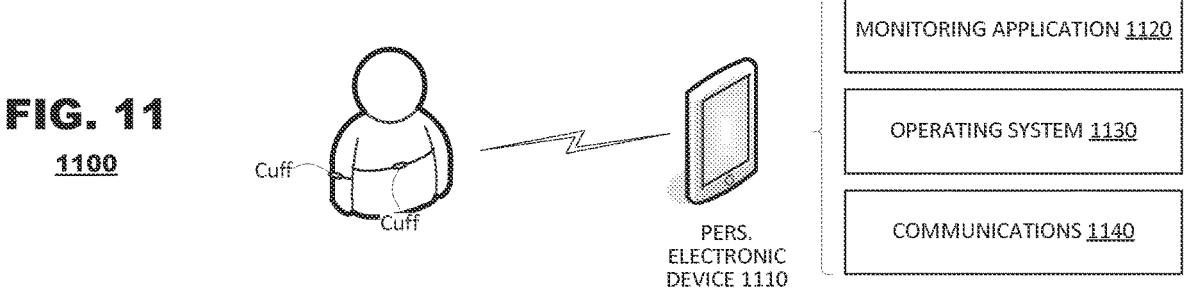
MONITORING APPLICATION 1120
OPERATING SYSTEM 1130
COMMUNICATIONS 1140
Cuff
Cuff
PERS. ELECTRONIC DEVICE 1110
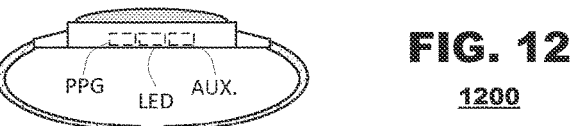
PPG  LED  AUX.
FIG. 12
1200
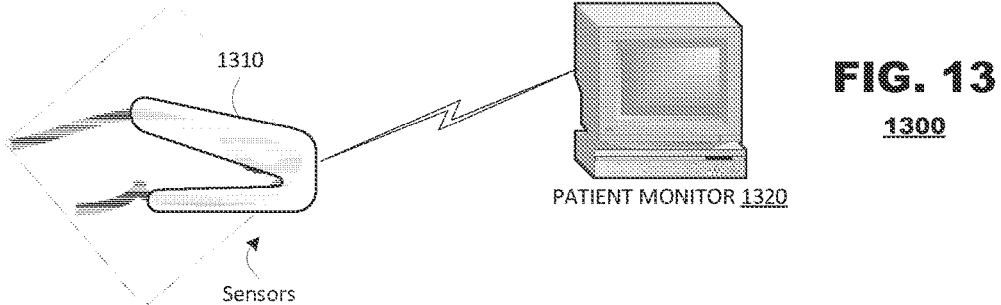
1310
Sensors
PATIENT MONITOR 1320
FIG. 13
1300

LOW FREQUENCY NOISE IMPROVEMENT IN PLETHYSMOGRAPHY MEASUREMENT SYSTEMS

CROSS-REFERENCE TO RELATED APPLICATIONS

This application is a divisional application and claims the benefit under 35 U.S.C. § 121, of U.S. patent application Ser. No. 14/500,129 filed Sep. 29, 2014 entitled, "LOW FRE-QUENCY NOISE IMPROVEMENT IN PLETHYSMOG-RAPHY MEASUREMENT SYSTEMS", and U.S. Provisional Application Ser. No. 61/954,301 filed Mar. 17, 2014 entitled, "LOW FREQUENCY NOISE IMPROVEMENT IN PPG MEASUREMENT SYSTEMS" of which both applications are incorporated herein by reference in their entirety.

FIELD OF INVENTION

The present invention relates to plethysmography ("PPG") detectors and other devices that detect biological events and, in particular, improving signal-to-noise ratios ("SNR") per unit of expended power that is used to gather PPG signals.

BACKGROUND

A plethysmograph detector is a device for measuring biological events within body tissue. Using a PPG detector, and other devices for detecting biological events, operate by measuring changes in transmission or diffuse reflectance from the body tissue or subject under active illumination.

The radiation used for measuring PPG signals can span wavelengths from blue to infrared. In classic applications, LEDs of two colors—often 660 nm and 940 nm—are used for measuring blood oxygen saturation. These devices are in large volume production and are readily available. In yet another application, a simple single-color LED—say at 940 nm—may be used to measure heart rate by measuring the periodic variation in a return signal. In some cases, a green LED is used to pick up variation in absorption caused by blood flow on the wrist.

FIG. 1 shows some of the common methods of measuring PPG signals. PPG signals are generated by measuring the changes in the transmission or diffuse reflectance of body tissue under active illumination by LED of a particular wavelength. The beating of the heart changes both the mechanical dimensions of the arteries and also blood volume in those arteries. These effects lead to variation in the received light intensity. FIG. 2 shows a typical PPG signal and estimates of the signal required to measure parameters such as blood oxygen.

There is developing interest to measure PPG signals continuously by incorporating PPG sensors/systems in devices that can be attached to a subject, for example, wrist band, watch, in-the-ear buds, etc. In such applications, these devices have to function with very low power and every photon emitted from the LED is precious as it is a drain on a battery. Furthermore, space constraints force the use of small photodiodes to collect diffuse light coming from the tissue. As a result, the signal is small and any reduction in noise of the system can be immediately applied to conserve battery power and increase the time to recharge or replace batteries.

Thus much attention has been paid to reduce the noise of the receiver systems and noise in the LED drive circuits.

Many noise reduction techniques for LED drivers and receivers require extra power. To make matters worse, many visible light LEDs themselves exhibit fairly large "1/f" noise in the generated light. This noise is a result of both 1/f noise in the LED driver as well as the physical mechanisms in the LED, such as the thermal fluctuations and the generation-recombination noise.

Since a heart beats at a relatively low frequency in the range of 0.5-5 Hz (30 to 300 beats per minute), this low frequency noise essentially limits the ability to measure the PPG signal. This becomes even more crucial for blood oxygen saturation (SpO2) systems where accurate determinations of both AC and DC components of the PPG signal must be made.

Accordingly, the inventor perceives a need in the art for PPG system that permits reduction of noise in PPG signals captured by such systems.

BRIEF DESCRIPTION OF THE DRAWINGS

FIG. 1a-1b are functional block diagrams of exemplary PPG systems.

FIG. 2 is a graph of a PPG signal and estimates of the signal required to measure parameters.

FIG. 11-13 illustrates various applications for sensor systems of embodiments of the present invention

DETAILED DESCRIPTION

Embodiments of the present invention provide at least one source of PPG radiation and at least one sensor for detection of PPG radiation. The source of PPG radiation emits a portion of the PPG radiation toward a subject and another portion along an optical path for direct communication between the source of PPG radiation and the sensor. The sensor may develop a profile against which measurements from other PPG sensors, which receive light returning from the subject, may be compared. From this comparison, new PPG signals may be generated that exhibit lower noise than the PPG signals output by PPG sensors. These noise mitigation techniques may be used advantageously by a PPG system to generate more accurate measurements and also to reduce power consumption by the radiation sources.

Figure 3:
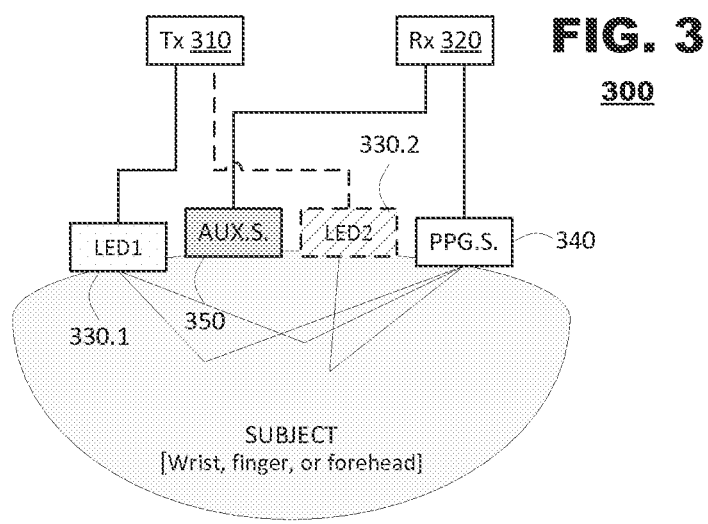
FIG. 3 is a functional block diagram of a PPG system according to an embodiment of the present invention.

FIG. 3 is a functional block diagram of transmission structures in a PPG system 300 according to an embodiment of the present invention. The system 300 may include a transmitter 310 that drives control signals to one or more LEDs 330.1, 330.2 of the system 300; a receiver 320 that receives signals from one or more sensors 340, 350 of the system; at least one LED 330.1 provided to transmit light toward the tissue of a subject; a PPG sensor 340 provided to receive light reflected from the tissue of a subject and to generate data signals therefrom; and an auxiliary sensor 350 provided to receive light from the LED(s) 330.1, 330.2 through a direct path (e.g., not via reflectance from the subject).

The LED(s) 330.1, 330.2, PPG sensor 340 and auxiliary sensor 350 may be provided on a common side of tissue of a subject.

The system 300 may have as few as a single LED 330.1 but, optionally, may include others (e.g., LED 330.2). In such an embodiment, there would be at least one auxiliary sensor 350 provided to receive light from each of the LEDs 330.1, 330.2 in the system. A single auxiliary sensor 350 may receive light from several LEDs 330.1, 330.2 as illustrated in FIG. 3 or, alternatively, the system 300 may include multiple auxiliary sensors (not shown), each of which receives light from a sub-set of the LEDs 330.1, 330.2 in the system.

The auxiliary sensor(s) 350 may be provided as detectors that are appropriate to detect the type of light emitted from the LED(s). In this regard, the auxiliary sensor(s) 350 may be provided as photodetectors, which are made from the same materials as the corresponding PPG sensors 340. Typical materials include silicon- and/or germanium-based sensors.

In the system 300 illustrated in FIG. 3, the LED(s) 330.1, 330.2 direct light toward the tissue of a subject for which PPG measurements are to be taken. LED light may be reflected from the tissue toward the PPG sensor 340 and captured as electrical signals. The receiver 320 may direct the electrical signals to other components (not shown) within the system 300.

Light from the LED(s) 330.1, 330.2 also may be received by the auxiliary sensor(s) 350 through a path that does not include the subject. The auxiliary sensor(s) 350 also may generate electrical signals from the light they receive. The receiver 320 may direct the electrical signals to other components (not shown) within the system 300. Signals from the auxiliary sensor(s) 350 may be used as a basis to remove noise from the signals generated by the PPG sensor 340.

The transmitter 310 may include driver circuitry and controllers to drive activation signals to the LED(s) 330.1, 330.2, which cause the LED(s) to illuminate as desired for the PPG application at hand. The transmitter 310, for example, may cause LEDs to illuminate on a pulsed basis or a continuous basis. In a multi-LED embodiment, illumination of LEDs may occur in a multiplexed fashion to permit PPG measurements to distinguish between reception of different kinds of light (for example, 660 nm light vs. 940 nm light).

The receiver 320 may include circuitry to generate signals appropriate for analysis. For example, the receiver 320 may include an analog front end, which may include filters and/or digitizers (not shown). The filters may eliminate signals from spurious frequencies from the sensors' outputs. Digitizers may sample the sensors' outputs and generate digital data therefrom.

Figure 4:
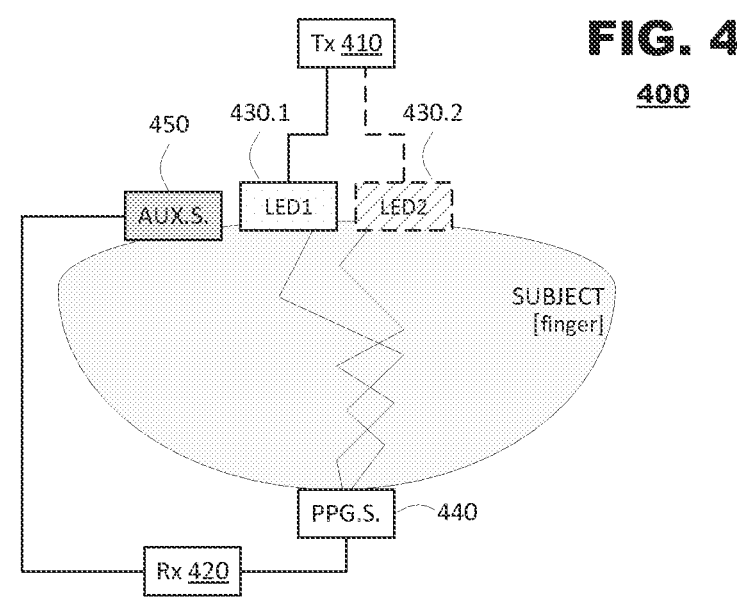
FIG. 4 is a functional block diagram of a PPG system according to an embodiment of the present invention.

FIG. 4 is a functional block diagram of transmission structures in a PPG system 400 according to another embodiment of the present invention. The system 400 may include a transmitter 410 that drives control signals to one or more LEDs 430.1, 430.2 of the system 400; a receiver 420 that receives signals from one or more sensors 440, 450 of the system; at least one LED 430.1 provided to transmit light toward the tissue of a subject; a PPG sensor 440 provided to receive light that passes through the tissue of a subject and to generate data signals therefrom; an auxiliary sensor 450 provided to receive light from the LED(s) 430.1, 430.2 through a direct path (e.g., not via reflectance or transmittance from the subject).

The LED(s) 430.1, 430.2 and auxiliary sensor 450 may be provided on a common side of tissue of a subject. The PPG sensor 440 may be provided on another side of the subject, approximately across from the LED(s) 430.1, 430.2.

The system 400 may have as few as a single LED 430.1 but, optionally, may include others (e.g., LED 430.2). In such an embodiment, there would be at least one auxiliary sensor 450 provided to receive light from each of the LEDs 430.1, 430.2 in the system 400. A single auxiliary sensor 450 may receive light from several LEDs 430.1, 430.2 as illustrated in FIG. 4 or, alternatively, the system 400 may include multiple auxiliary sensors (not shown), each of which receives light from a sub-set of the LEDs 430.1, 430.2 in the system.

The auxiliary sensor(s) 450 may be provided as detectors that are appropriate to detect the type of light emitted from the LEDs In this regard, the auxiliary sensor(s) 450 may be provided as photodetectors, which are made from the same materials as the corresponding PPG sensors 440. Typical materials include silicon- and/or germanium-based sensors.

In the system 400 illustrated in FIG. 4, the LED(s) 430.1, 430.2 direct light toward the tissue of a subject for which PPG measurements are to be taken. LED light may pass through the subject's tissue toward the PPG sensor 440 and may be captured as electrical signals. The receiver 420 may direct the electrical signals to other components (not shown) within the system 400.

Light from the LED(s) 430.1, 430.2 also may be received by the auxiliary sensor(s) 450 through a path that does not traverse the subject's tissue. The auxiliary sensor(s) 450 also may generate electrical signals from the light they receive. The receiver 420 may direct the electrical signals to other components (not shown) within the system 400. Signals from the auxiliary sensor(s) 450 may be used as a basis to remove noise from the signals generated by the PPG sensor 440.

The transmitter 410 may include driver circuitry and controllers to drive activation signals to the LED(s) 430.1, 430.2, which cause the LED(s) to illuminate as desired for the PPG application at hand. The transmitter 410, for example, may cause LEDs to illuminate on a pulsed basis or a continuous basis. In a multi-LED embodiment, illumination of LEDs may occur in a multiplexed fashion to permit PPG measurements to distinguish between reception of different kinds of light (for example, 660 nm light vs. 940 nm light).

The receiver 420 may include circuitry to generate signals appropriate for analysis. For example, the receiver 420 may include an analog front end, which may include filters and/or digitizers (not shown). The filters may eliminate signals from spurious frequencies from the sensors' outputs. Digitizers may sample the sensors' outputs and generate digital data therefrom.

Figure 5:
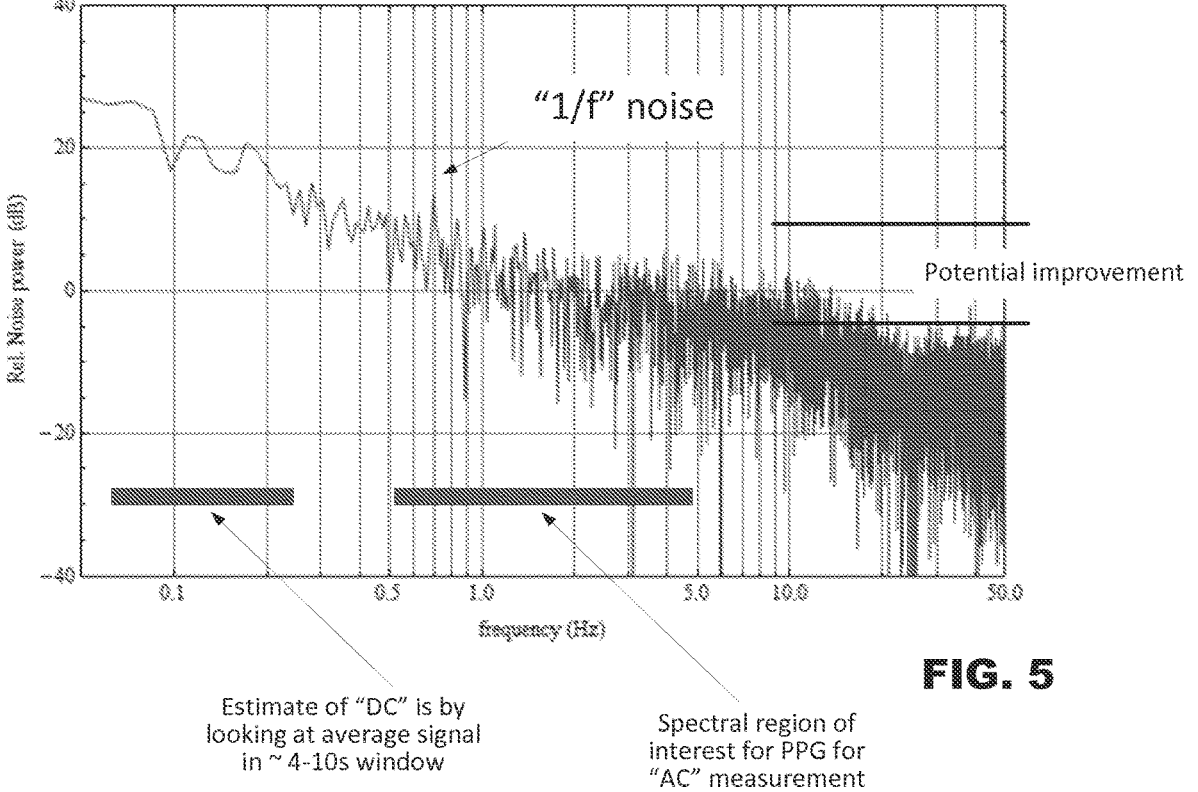
FIG. 5 is a graph showing a power spectrum of measurements taken from a PPG system according to an embodiment of the present invention.

FIG. 5 is a graph showing an exemplary power spectrum of measurements taken from a PPG measurement system using a green LED. In this particular case, an LED was pulsed with an activation signal of approximately 3 μs duration. A PPG sensor measured reflections from a stationary gray card over a duration of approximately 5 seconds.

This data was measured at 100 Hz. The power spectrum of the signal illustrates frequency distribution of noise for such PPG sensors.

The power spectrum indicates that there is a large increase in noise at low frequencies, called the 1/f noise. This ubiquitous noise limits a system's ability to measure PPG signal in the 0.4 Hz-5 Hz spectral window.

For a simple heart rate measurement, lower intensity PPG signals can be measured if the corresponding 1/f noise is lowered. For measurement requiring quantitative estimate of the "DC" and the "AC" portion of the signal, 1/f noise corrupts both the DC and the AC estimates. Lines are marked on the figure showing potential improvement.

An auxiliary sensor (such as in FIG. 3 or 4) may be placed next to an LED in such a way so as to predominantly measure the light output of the LED at the same time as the PPG sensor measures the PPG signal. This may be accomplished for any driving pattern applied to an LED, for example, an LED that emits light in a pulsed fashion or one that emits light continuously. The auxiliary sensor may detect an estimate of the actual light generated by the LED that illuminates the subject. This allows direct measurement of the tissue system free of additional low frequency noise generated by the transmitter which includes both the LED and the LED driver. The auxiliary sensor's measurement may be made by the same receiver system as the receiver used for measuring the main PPG signal after transmission or reflection from the tissue. A new signal may be formed as:

$$L = \frac{L_{PPG}}{L_t} \qquad \text{Eq. 1}$$

Where $L_{PPG}$ represents the measurement from the PPG sensor and $L_t$ represents the measurement from the auxiliary sensor.

This new signal should have reduced 1/f noise in the spectral region dominated by 1/f noise of the transmitter. And, because the resultant signal exhibits lower noise, systems that employ such techniques can achieve improved performance in other areas of the system, for example, by requiring lower power to drive the LEDs. Improvements in individual implementations likely will vary by LED (for example, due to variations in type, process, manufacturer etc.) as well as by the LED driver. Note that doubling the LED's effective power due to reduction of 1/f noise leads to between 3 dB-6 dB (max) improvement in SNR. The 3 dB improvement can occur if the performance is shot noise limited by the photodetector and a 6 dB improvement can occur when performance is limited by the internal receiver noise. Thus, potential improvements of approximately 10 dB may arise in specific implementations, which represent a substantial savings in power.

This auxiliary detector can be used in a variety of configurations that are used for measurement of PPG signals. Examples include:

A low power module for small form factor peripheral devices such as a wristband, a watch, or an ear bud.

A very high SNR wireless monitoring system for hospitals and health care providers.

Measurement of multiple blood parameters in which accurate determination of AC and DC parts of the PPG signals are measured at multiple wavelengths such as pulse oximetry.

Figure 6:
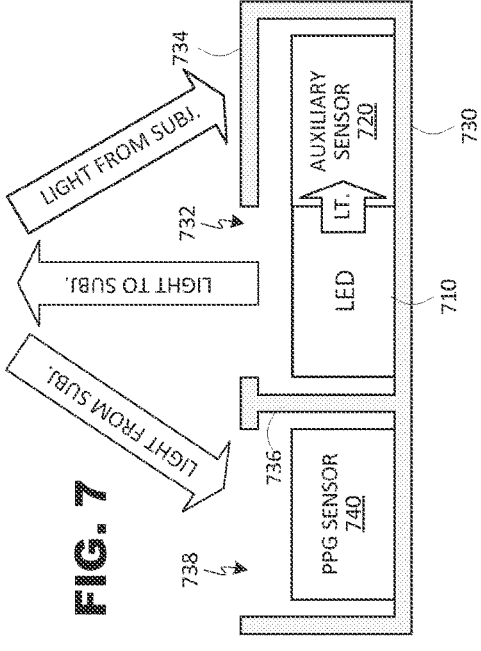
FIG. 6 illustrates a configuration of a PPG system according to an embodiment of the present invention.
Figure 7:
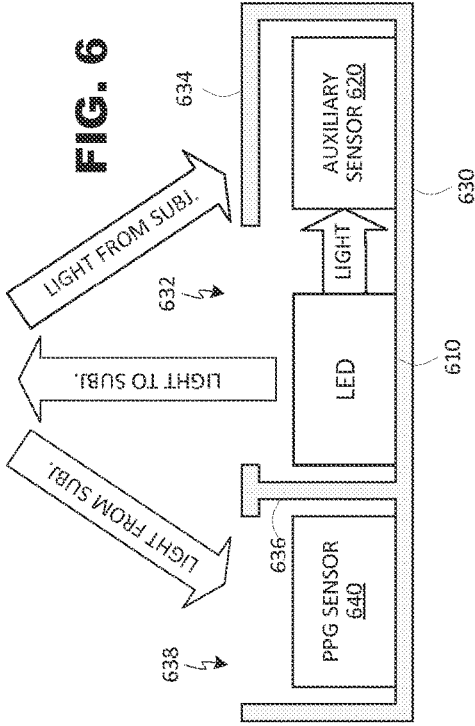
FIG. 7 illustrates a configuration of a PPG system according to an embodiment of the present invention.
Figure 8:
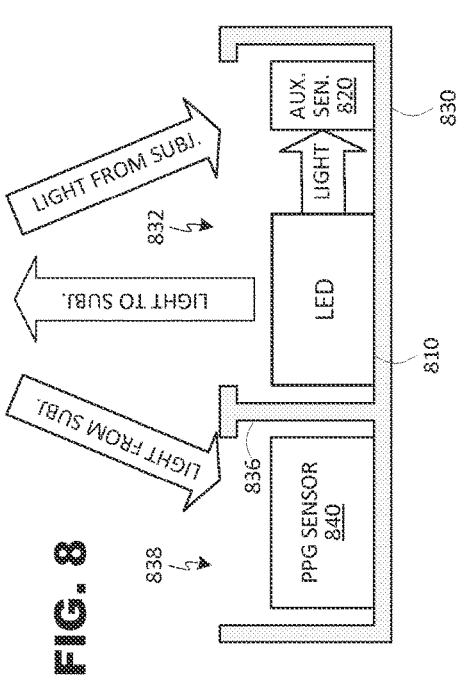
FIG. 8 illustrates a configuration of a PPG system according to an embodiment of the present invention.

FIGS. 6-8 illustrate configurations of LEDs, auxiliary sensors and PPG sensors according to different embodiments of the present invention. In each instance, an LED and an auxiliary sensor may be provided in proximity to each other to permit light from the LED to be received by the auxiliary sensor via an optical transmission path that does not traverse the subject's tissue.

FIG. 6 illustrates an embodiment in which an LED 610 and an auxiliary sensor 620 are provided on separate semiconductor substrates. The LED 610 and auxiliary sensor 620 are provided in a common housing 630 that provides mechanical support for the LED 610 and sensor 620. The housing 630 may define an aperture 632 for light from the LED 610 to escape the housing to illuminate a subject. The housing 630 also may define a shield 634 to inhibit light that is reflected from the subject from reaching the auxiliary sensor. The housing 630 may be made of a material that is opaque to the form of light emitted from the LED 610.

The LED 610 and auxiliary sensor 620 may be placed proximate to each other to allow light from the LED 610 to be received by the auxiliary sensor 620 along an optical path that does not traverse the subject.

In a reflective PPG system, a PPG sensor 640 may be provided in the housing 630 along with the LED 610 and the auxiliary sensor 620. Ideally, the PPG sensor 640 only would receive LED light that is reflected from the subject. The housing 630 may include a partition 636 that inhibits LED light from reaching the PPG sensor 640 along a direct path. It also may include an aperture 638 that allows reflected light from the subject to be captured by the PPG sensor 640.

FIG. 7 illustrates an embodiment in which an LED 710 and an auxiliary sensor 720 are provided on a common semiconductor substrate. The LED 710 and auxiliary sensor 720 are provided in a common housing 730 that provides mechanical support for the LED 710 and sensor 720. The housing 730 may define an aperture 732 for light from the LED 710 to escape the housing to illuminate a subject. The housing 730 also may define a shield 734 to inhibit light that is reflected from the subject from reaching the auxiliary sensor. The housing 730 may be made of a material that is opaque to the form of light emitted from the LED 710.

The LED 710 and auxiliary sensor 720 may be provided on a common semiconductor substrate which allows a portion of light from the LED 710 to be received by the auxiliary sensor 720 directly. This light along the direct optical path between the LED 710 and the auxiliary sensor 720 does not traverse the subject.

In a reflective PPG system, a PPG sensor 740 may be provided in the housing 730 along with the LED 710 and the auxiliary sensor 720. Ideally, the PPG sensor 740 only would receive LED light that is reflected from the subject. The housing 730 may include a partition 736 that inhibits LED light from reaching the PPG sensor 740 along a direct path. It also may include an aperture 738 that allows reflected light from the subject to be captured by the PPG sensor 740.

FIG. 8 illustrates an embodiment in which an LED 810 and an auxiliary sensor 820 are provided on separate semiconductor substrates. The LED 810 and auxiliary sensor 820 are provided in a common housing 830 that provides mechanical support for the LED 810 and sensor 820. The housing 830 may define an aperture 832 for light from the LED 810 to escape the housing to illuminate a subject. In this embodiment, the housing 830 need not include a shield as in FIG. 6 to inhibit reflected light from the subject from reaching the auxiliary sensor 820. The housing 830 may be made of a material that is opaque to the form of light emitted from the LED 810.

The LED 810 and auxiliary sensor 820 may be placed proximate to each other to allow light from the LED 810 to be received by the auxiliary sensor 820 along an optical path that does not traverse the subject. The auxiliary sensor 820 may be provided of a size that is smaller than sizes of PPG sensors used in common PPG detection systems. For example, in systems having PPG sensors with 1-4 mm$^2$ effective surface area for light capture, a corresponding auxiliary sensor 820 may be provided with approximately 50 μm$^2$ effective surface area for light capture (e.g., $\frac{1}{20}^{th}$-$\frac{1}{80}^{th}$ the size of a PPG sensor). In such embodiments, it is expected that noise cancellation estimates may be obtained even if the auxiliary sensor 820 receives reflected light from a subject because the LED light received by the auxiliary sensor 820 along a direct optical path should have much larger magnitude than LED light received via reflection from the subject.

In a reflective PPG system, a PPG sensor 840 may be provided in the housing 830 along with the LED 810 and the auxiliary sensor 820. Ideally, the PPG sensor 840 only would receive LED light that is reflected from the subject. The housing 830 may include a partition 836 that inhibits LED light from reaching the PPG sensor 840 along a direct path. It also may include an aperture 838 that allows reflected light from the subject to be captured by the PPG sensor 840.

FIGS. 6-8 illustrate packaging applications that are suitable for use with reflective PPG systems such as in FIG. 3. The relationships between the LEDs and auxiliary sensors illustrated in FIGS. 6-8 also find application in transmissive systems such as those shown in FIG. 4. In the transmissive systems, however, the relationships between the LEDs and PPG sensors likely would vary from those illustrated in FIGS. 6-8. As illustrated in FIG. 4, the PPG sensors likely would be placed elsewhere on tissue being measured.

As discussed, the auxiliary sensors may provide a signal that measures the actual light output used to measure the environment (finger etc.) such that variation in the LED's output can be minimized (ideally, eliminated) from the PPG sensors' final measurements. The auxiliary sensors' output also can reduce or eliminate effects of variations in other aspects of the electrical environment. For example, in practice when sensors are manufactured and deployed, it is quite common that power supply variations, which can have complex time-varying patterns, can cause both LED outputs and receiver measurements to vary. While a good circuit designers try to include high power supply rejection ratios in their designs, there is a limit how well they can perform and especially at all frequencies. Use of an auxiliary detector can provide immunity to variations in LED output (no matter its origin) but also to changes in the receiver circuit from electrical noise since both the auxiliary detector and the main PPG detectors are measured by the same or receiver system (although not necessarily same amplifiers).

The noise mitigation techniques described hereinabove may lead to the simplification of the design of LED drivers that with less attention paid to/f noise and provide further conservation of battery capacity. This can lead to highly efficient designs such as the one illustrated in FIG. 9.

Figure 9A:
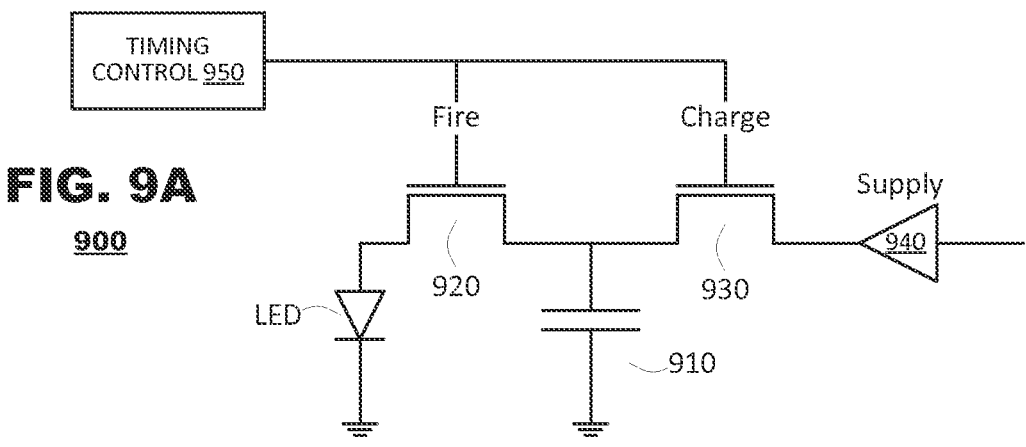
FIG. 9a-9c illustrates an LED driver circuit according to various embodiments of the present invention.
Figure 9B:
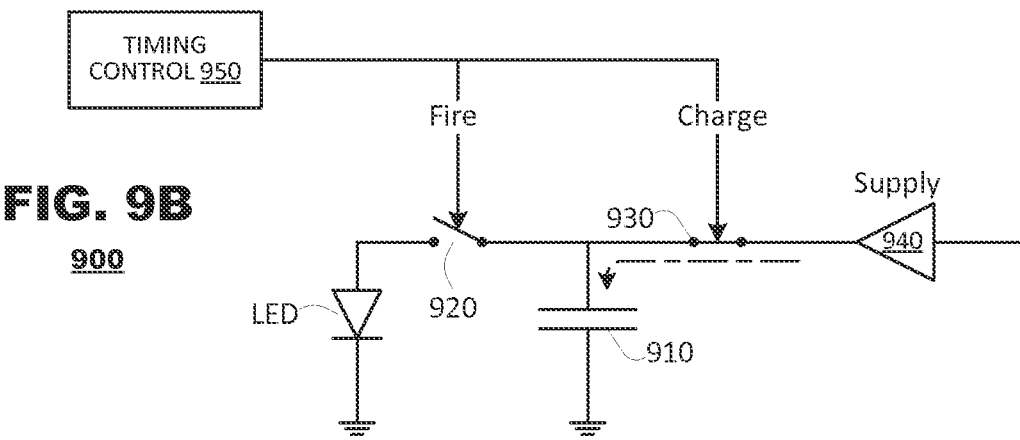
Figure 9C:
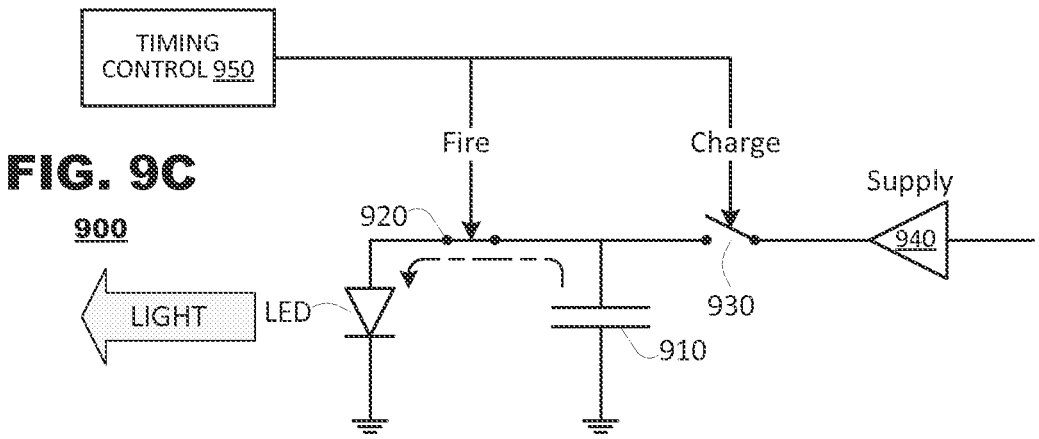

FIG. 9(*a*) illustrates an LED driver circuit 900 according to an embodiment of the present invention. The circuit 900 may include a capacitor 910; a pair of transistors 920, 930; a voltage supply 940; and a timing controller 950.

The transistors 920, 930 may control operation of the LED driver through two phases of operation: a charging phase and an LED activation phase. During the charging phase, charge from the supply 940 may be stored by the capacitor 910. During the LED activation phase, charge from the capacitor 910 may be applied to the LED to cause it to illuminated (colloquially, the LED "fires"). The timing controller 950 is a logic circuit that controls operation of the transistors as the driver circuit 900 processes through these phases.

FIGS. 9(*b*) and 9(*c*) illustrate operation of the driver circuit 900 through the two phases. In these drawings, the transistors 920, 930 are illustrated as switches to illustrate electrical flow among the components.

FIG. 9(*b*) illustrates operation of the driver circuit 900 during the charge phase. During this phase, switch 930 is illustrated as closed and switch 920 is illustrated as open. Charge from the supply 940 may flow to the capacitor 910, thereby charging the capacitor 910 to a predetermined level. The duration of the charge phase may be controlled by the timing controller 950 and may be programmed to suit individual application needs.

FIG. 9(*c*) illustrates operation of the driver circuit during the activation phase. During this phase, switch 920 is closed and switch 930 is open. Charge from the capacitor 910 is applied to the LED, causing it to illuminate. The duration of the activation phase also may be controlled by the timing controller 950 and may be programmed to suit individual application needs. The LED, therefore, may emit a pulse of light whose duration is determined by the duration of the activation phase. The capacitor 910 may be sized to store an amount of charge sufficient to cause the LED to remain illuminated for the entirety of the activation phase.

In such a design, there might be substantial variation in the total charge "dumped" into the LED from one pulse to next depending on the design of the supply circuit 940 (a trickle charging circuit) and other ambient factors. The noise mitigation techniques illustrated above can mitigate the impact of such pulse-to-pulse variation since the LED output itself is directly measured and compensated as discussed in Eq. 1.

Such trickle charging circuit would result in a low average current from the battery while supplying large LED peak current for a short time which results in a quick measurement by an analog front end (AFE) within a receiver. This results in a net saving of battery charge as battery capacity is not degraded by large transients generated by LED pulse. At the same time, a short intense LED pulse intrinsically improves the SNR of the receiver while the addition of the auxiliary channel to measure actual LED output results in suppression of low frequency noise.

Figure 10:
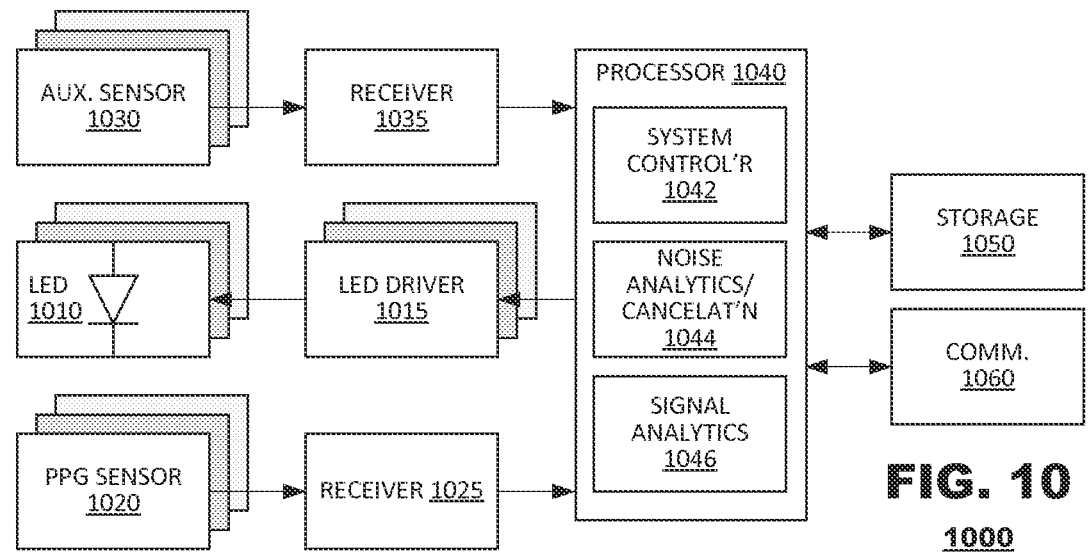
FIG. 10 is a functional block diagram of a PPG measurement system according to an embodiment of the present invention.

FIG. 10 is a functional block diagram of a PPG measurement system 1000 according to an embodiment of the present invention. The system 1000 may include one or more LEDs 1010; one or more LED drivers 1015 to control activation of the LED(s) 1010; one or more PPG sensors 1020; one or more receivers 1025 for the PPG sensors 1020; one or more auxiliary sensors 1030; one or more receivers 1035 for the auxiliary sensors 1030; and a processor 1040 that includes functional units devoted to overall system control 1042, signal analytics 1044 and noise analytics 1046. Optionally, system 1000 may include storage 1050 and/or a communication transceiver 1060.

The LED drivers 1015 and LEDs 1010 may operate as discussed above. The drivers 1015 may generate activation signals to cause the LEDs 1010 to illuminate in a predetermined fashion, for example, generating light on a pulsed basis or continuous basis.

The PPG sensors 1020 and receivers 1025 also may operate as discussed above. The PPG sensors 1020 may generate electrical signals from light incident thereon and the receivers 1025 may perform processing operations on such signals, for example, filtering and digitization.

The auxiliary sensors 1030 and receivers 1035 may operate as discussed above. The auxiliary sensors 1030 may generate electrical signals from light incident thereon and the receivers 1035 may perform processing operations on such signals, for example, filtering and digitization. The receivers 1025, 1035 are illustrated in FIG. 10 as separate components merely for convenience; if desired, they may share circuit components such as analog-to-digital converters.

The system controller 1042 may represent a control process to manage overall operation of the system 1000. The noise analytics block 1046 may represent processes to be performed by the processor 1040 to estimate and perhaps categorize LED noise from signals output by the auxiliary sensor 1030. For example, as an alternative to noise mitigation discussed in Eq. 1, the noise analytics block 1046 may generate noise estimates from signals received from the auxiliary sensors 1030 according to noise cancellation algorithms. The noise analytics block 1046 may generate an anti-noise signal that is applied to signals received from the PPG sensors 1020 in a noise cancellation process. In this embodiment, noise cancellation processes may scale noise components and apply them subtractively to the PPG signals in the following form:

$$L = L_{PPG} - k * L_{noise} \qquad \text{Eq. 2}$$

Where $L_{PPG}$ represents the signal received from the PPG sensors 1020, $L_{noise}$ represents the anti-noise signal generated by the noise analytics block 1046, and k represents a scaling factor to reduce noise in $L_{PPG}$.

The signal analytics block 1046 may perform processing of noise-processed signals according to PPG techniques. For example, rather than store data representing the processed signal themselves, the signal analytics block 1046 may derive data representing heart rate, cardiac rhythms, breathing rate, hypo- and/or hypervolemia conditions and other indicators normally captured by PPG monitoring systems.

The system 1000 also may include storage units 1050 (e.g., electrical, magnetic and/or optical memory systems) to store data from the processor and/or communication devices 1060 (e.g., wireless, infra-red or other communicators) to report data to other medical devices.

FIGS. 11-13 illustrate different applications for sensor systems of the foregoing embodiments.

In the embodiment illustrated in FIG. 11, for example, the sensor systems may be integrated into a cuff that may be worn about some portion of a subject's body. Cuffs are illustrated as provided about the arm or the chest of a subject. Alternatively, they may be integrated into headphones that place sensors in contact with the ears, into headbands that may place the sensors in contact with skin about the forehead, into wristbands, etc. The sensors may communicate with a personal electronic device 1110 via wireless communications transceivers such as Bluetooth.

The personal electronic device 1110 may include a monitoring application 1120 to analyze signals reported to it by the sensors. The monitoring application 1120 may interface with an operating system 1130 and communication devices 1140 within the electronic device 1110 to perform its operations.

The personal electronic device 1100 may be provided as a smartphone, tablet computer, personal heartrate monitor or other electronic device that collects physiological data regarding the subject. The PPG sensor systems discussed herein may be integrated with other fitness sensors that gather physiological data through other means.

In the embodiment illustrated in FIG. 12, the sensor systems may be integrated into a wristwatch or other personal accessory that is worn on a subject's body in contact with some portion of the subject's tissue. In addition to sensors, the accessory may include processors to perform analytics of the signals generated by the sensors and to derive PPG data. The wristwatch may have a display and associated controls that may display derived PPG data on command.

FIG. 13 illustrates application of the sensor systems in a medical environment. In this embodiment, the sensors may be integrated into a sheath 1310 that is affixed to some portion of a patient's tissues (in this example, the patient's finger). The sensors may generate signals that are reported to monitoring equipment 1320 by wire-line or wireless communication link. The patient monitor 1320 may include analytics to derive physiological data from the signals reported to it by the sensors. The patient monitor 1320 also may support other types of sensors (not shown) and may generate other analytics therefrom.

Numerous specific details have been set forth herein to provide a thorough understanding of the embodiments. It will be understood by those skilled in the art, however, that the embodiments may be practiced without these specific details. In other instances, well-known operations, components and circuits have not been described in detail so as not to obscure the embodiments. It can be appreciated that the specific structural and functional details disclosed herein may be representative and do not necessarily limit the scope of the embodiments.

Various embodiments may be implemented using hardware elements, software elements, or a combination of both. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

Some embodiments may be implemented, for example, using a computer-readable medium or article which may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

I claim:

1. A method for mitigating pink noise in a PPG signal received from a subject, the method comprising:

externally illuminating body tissue of a subject with light emitted from a radiation source;

measuring, by a first sensor, a first portion of the light returned from the body tissue;

generating a first signal based on a measurement by the first sensor;

measuring, by an auxiliary sensor, a portion of the light whose optical path does not traverse the body tissue;

blocking, by a shield of a housing that houses the radiation source, the first sensor, and the auxiliary sensor, a second portion of the light returned from the body tissue in an optical pathway between the body tissue and the auxiliary sensor;

generating an auxiliary signal based the measurement by the auxiliary sensor; and removing a common mode from the first signal based at least on the auxiliary signal.

2. The method of claim 1, further comprising determining the PPG signal.

3. A sensor system, comprising:

a source of photoplethysmographic (PPG) radiation;

a first sensor for detection of PPG radiation;

an auxiliary sensor for detection of PPG radiation; and a housing that accommodates the source, the first sensor, and the auxiliary sensor, wherein the housing defines an aperture for emission of a portion of the PPG radiation from the source toward body tissue of a subject and an optical path for direct communication of another portion of the PPG radiation from the source to the auxiliary sensor.

4. The sensor system of claim 3, wherein the first sensor is for detecting PPG radiation returned from body tissue of the subject.

5. The sensor system of claim 3, wherein the housing accommodates the first sensor and defines a second aperture therefor.

6. The sensor system of claim 3, wherein the housing comprises a portion for housing the source and the auxiliary sensor, and another portion for housing the first sensor at least partially under the aperture.

7. The sensor system of claim 3, further comprising a noise cancellation system for (i) generating noise estimates from signals received from the auxiliary sensor according to one or more noise cancellation algorithms and (ii) generating an anti-noise signal that is applied to signals received from the first sensor in a noise cancellation process.

8. The sensor system of claim 3, wherein an effective surface area of the auxiliary sensor is smaller than an effective surface area of the first sensor.

9. The sensor system of claim 8 wherein a ratio of an effective area of the auxiliary sensor to an effective area of the first sensor is approximately between $\frac{1}{20}$th and $\frac{1}{80}$th.

10. The sensor system of claim 3, wherein the housing further defines a shield to block the PPG radiation reflected from the subject to the auxiliary sensor.

11. The sensor system of claim 6, wherein the housing includes a partition to inhibit transmission of the another portion of the PPG radiation to the first sensor.

12. A system, comprising:

a photoplethysmographic (PPG) measurement system including: a source of PPG radiation;

a pair of sensors for detecting PPG radiation, a first sensor to detect PPG radiation that traverses body tissue of a test subject and a second sensor to detect PPG radiation from the source along a direct optical path, from the source of PPG radiation to second sensor, that does not traverse the body tissue of the test subject; and a processor operative to:

manage operation of the system;

receive signals-based output signals from the pair of sensors; and apply noise management logic to the signals-based output signals, wherein the noise management logic includes algorithms based on the signals-based output signals from the pair of sensors.

13. The system of claim 12, wherein the first sensor is positioned to detect PPG radiation reflected by the body tissue of the test subject.

14. The system of claim 12, wherein the first sensor is positioned to detect PPG radiation transmitted through the body tissue of the test subject.

15. The system of claim 12, wherein the noise management logic reduces noise in an output of the first sensor based on an output from the second sensor.

16. The system of claim 15, wherein the noise management logic reduces noise in the output of the first sensor based on:

$$L = L_{PPG} - k^* L_{noise}$$

where $L_{PPG}$ represents the output of the first sensor, $L_{noise}$ represents a noise estimate derived from the second sensor, and k represents a scaling factor to reduce noise from $L_{PPG}$.

17. The system of claim 12, wherein the noise management logic reduces noise in an output of the first sensor based on:

where $L_{PPG}$ represents a measurement from the first sensor and Lt represents a measurement from the second sensor.

18. The system of claim 12, wherein the pair of sensors communicate with the processor via at least one wireless communication link.

19. The system of claim 12, further comprising a monitoring device provided in communication with the processor via a wireless communication link.

20. The system of claim 12, wherein the system is at least one of a pulse oximetry measurement system and heart rate monitoring system.

* * * * *